United States Patent [19]

D'Angelo et al.

[11] Patent Number: 5,412,990
[45] Date of Patent: May 9, 1995

[54] METHOD FOR MEASURING CEMENT THICKENING TIMES

[75] Inventors: Ralph D'Angelo, New Fairfield; Thomas Plona, New Milford; Lawrence M. Schwartz, Westport, all of Conn.; Peter Coveney, Theydon Bois, England

[73] Assignee: Schlumberger Technology Corporation, New York, N.Y.

[21] Appl. No.: 854,551

[22] Filed: Mar. 20, 1992

[51] Int. Cl.$^6$ .................. G01H 5/00; G01N 9/24; G01N 29/18
[52] U.S. Cl. ........................ 73/597; 374/53; 73/594
[58] Field of Search .............. 73/594, 596, 597; 374/53

[56] References Cited

U.S. PATENT DOCUMENTS

| | | | |
|---|---|---|---|
| 3,537,541 | 11/1970 | Desai et al. | 73/597 |
| 4,259,868 | 4/1981 | Rao et al. | 73/597 |
| 4,377,087 | 3/1983 | Rodot | 73/597 |
| 5,265,461 | 11/1993 | Steiger et al. | 73/597 |

OTHER PUBLICATIONS

Ultrasonic Testing of Materials by Josef Krautkrämer and Herbert Krautkrämer, (Mar. 1977) Sections 1.1, and 1.2, pp. 5–12.
Hannant, et al., Setting behavior of cement pastes containing admixtures determined from shear modulus tests, *University of Surrey: Dept. of Civil Engineering*, Guildford, Surrey GU2, 5, England.
Ultrasonic Cement Analyzer, *Halliburton Services*, Manual No. 458.9728.
Stepisnik, et al., Measurement of Cement Hydration by Ultrasonics, *Ceramic Bulletin*, 60, pp. 481–483 (1981).
Keating, et al., Comparison of Shear Modulus and Pulse Velocity Techniques to Measure the Build-up of Structure in Fresh Cement Pastes Used in Oil Well Cementing, *Cement and Concrete Research*, vol. 19, pp. 554–566 (1989).
Hannant, D. J. and Keating, J., Equipment for Assessing the Development of Structure in Fresh Cement Pastes by the Measurement of Shear Modulus, *Pergamon Press, Ltd.*, 0008-8846/85, pp. 605–608 (1985).

*Primary Examiner*—Hezron E. Williams
*Assistant Examiner*—Rose M. Finley
*Attorney, Agent, or Firm*—Leonard W. Pojunas

[57] ABSTRACT

A method and apparatus for determining the setting time of a cement slurry. An acoustic shear wave signal is generated and introduced at a first location in the slurry. The signal is monitored at a second location for direct transmission of the shear wave signal. The time of first detection is determined at the second location which is taken as the setting time of the slurry.

19 Claims, 6 Drawing Sheets

METHOD FOR MEASURING CEMENT THICKENING TIMES

FIELD OF THE INVENTION

The present invention relates to a method of determining the setting time of a cement slurry. In particular, the invention measures a value which can be related to the American Petroleum Institute (API) "thickening time" of a cement slurry for oilwell cementing operations, although it is not restricted to this.

BACKGROUND OF THE INVENTION

Oilwell cementing operations are either 'primary', done in the course of drilling a well, or 'secondary' (also termed 'remedial'), for remedying deficiencies in primary cementing or to alter the well prior to production. Examples of 'secondary' cementing processes are 'squeeze cementing', in which a cement slurry is forced through holes or slits in the casing into voids or porous rock formations, and 'plug cementing', during which a small volume of cement slurry is placed in the wellbore to prevent loss of drilling fluid during the drilling phase or to seal off a depleted zone during the production phase.

The basic component of cements in use today is so-called 'ordinary Portland cement', whose raw ingredients are lime, silica, alumina and iron oxide. A pulverised blend of these raw materials is fed into a rotating kiln where temperatures as high as 1500° C. produce a molten mixture; on cooling, one is left with four principle mineral phases: 'alite' (tricalcium silicate, abbreviated as $C_3S$); 'belite' (dicalcium silicate $C_2S$); 'aluminate' (tricalcium aluminate, $C_3A$); and 'ferrite' (tetracalcium aluminoferrite, $C_4AF$). These four phases are taken from the kiln as a 'clinker', which is subsequently ground with gypsum (calcium sulphate) to produce ordinary Portland cement. The main chemical criterion for classifying Portland cements is the relative proportion of the four principle clinker phases.

Specifications for oilwell cements have been established by the API. There are currently eight classes of API Portland cement, designated Class A through H. These are classified according to the depth to which they are placed, and the temperatures and pressures to which they are exposed. Other physical parameters which appear in the API specification include the fineness of the cement powder and the performance of the cement slurry and set cement under standard tests. The performance tests include measurements of setting time, compressive strength, expansion and free water.

Because of the criticality of the setting time of a cement slurry and because of the complex nature of cement slurry compositions, it is necessary to determine the setting time for a given slurry composition experimentally before the slurry can be used in the field. The conventional method for estimating the setting time of a slurry is the API "thickening time" determined by placing a sample of the slurry in a consistometer in which a bob is rotated at elevated pressure and temperature and to measure the torque required to rotate the bob of the consistometer, the time at which the torque increases to 100 Bearden units being defined as the thickening time.

The thickening of cement is the result of the hydration process and it has been proposed to use ultrasonic measurement to monitor such processes. The article by Stepinsnik, Lukac and Loeuvacu in Ceramic Bulletin, 60, 481 (1981) describes the measurement of the reflection coefficient for ultrasonic shear waves in hydrating cement pastes. The reflected signals depend on several unknowns and must be processed to yield an estimate of the shear modulus. The article by Keating, Hamant and Hibbert in *Cement and Concrete Research*, Vol 19, pp 554–566, (1989) describes the measurement of the development of a shear modulus in hydrating cement paste by static methods.

The Ultrasonic Cement Analyzer from EG&G Chandler Engineering, Tulsa, Okla. USA, monitors the setting of cements by directly transmitting a compressional ultrasonic signal through a slurry to measure the development of compressional strength of the setting cement. This device also provides an indicator of "thickening time" based on a threshold detection of changes in compressional velocity in the slurry.

OBJECT AND SUMMARY OF THE INVENTION

It is an object of the present invention to provide a method of determining relatively accurately, the setting time of a cement slurry using an acoustic method.

In accordance with the present invention, there is provided a method of determining the setting time of a cement slurry. The steps include:
 a) generating an acoustic shear wave signal at a first location in the slurry;
 b) monitoring the slurry at a second location for direct transmission of the shear wave signal through the slurry; and
 c) determining the time at which shear wave energy begins to propagate through the slurry.

The present invention has the advantage that the direct transmission of the ultrasonic shear signals is measured. By contrast, the system developed by Stepinsik et al. measures reflected signals which depend on several unknowns, and must be processed to yield an estimate of the shear modulus. The setting time determined by the present invention can be directly related to the corresponding API thickening time.

The method comprises the generation of ultrasonic shear (S) and compressional (P) waves in the slurry under test. The detection of the development of a transmitted S wave signal and the corresponding increase in velocity of the transmitted P wave indicating the onset of thickening of the slurry.

The invention also provides an apparatus for measuring the setting time of a cement slurry comprising a body defining a cavity for containing the cement slurry, means for generating an ultrasonic shear wave signal mounted on one side of the cavity, means for receiving the shear wave signal mounted opposite the means for generating the signal, and means for recording the development with time of a transmitted shear wave signal through the slurry. The body can be a closed cell or a flow line and the means for generating and receiving the shear wave signal are typically transducers mounted in a wall of the body.

BRIEF DESCRIPTION OF THE FIGURES

The present invention will now be described, by way of example, with reference to the accompanying drawings, in which.

DETAILED DESCRIPTION OF THE FIGURES

Figure 1:
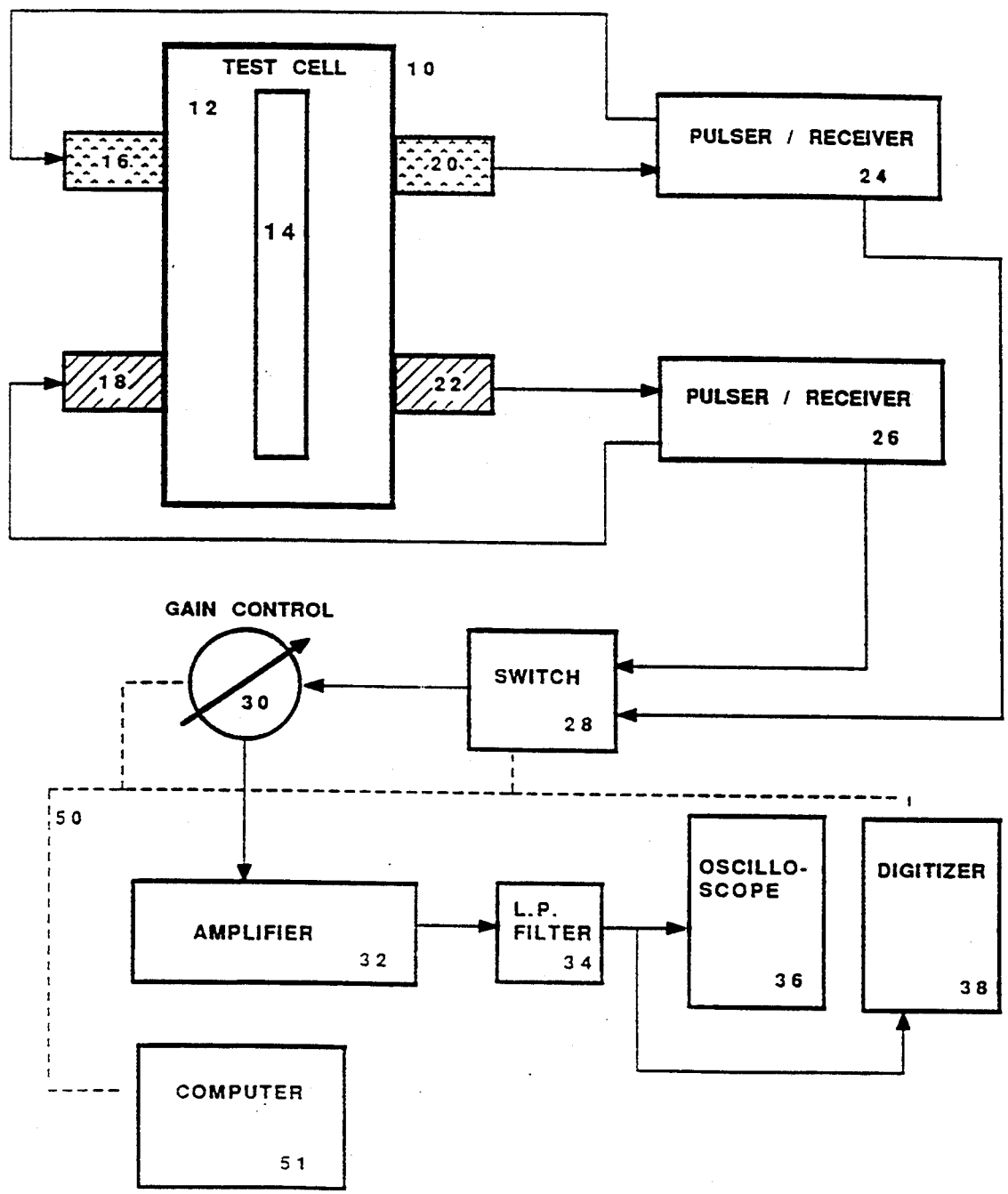
FIG. 1 shows a schematic diagram of a system for measuring the thickening time of a cement slurry.

FIG. 1 shows a system arranged for laboratory use although it will be appreciated that such a system might be easily adapted for rigsite use. The system comprises a test cell 10 having walls 12 formed from Lucite (i.e., poly methyl methacrylate) of approximately 25 mm thickness and defining a cavity 14 of dimensions 150 mm ×125 mm ×12.5 mm. A pair of transmitter transducers 16, 18 are mounted on the outside of the cell 10 for transmitting ultrasonic P and S wave signals respectively. A pair of receiver transducers 20, 22 are mounted on the opposite side of the cell 10 aligned with the transmitter transducers 16, 18 so as to receive the transmitted signals such that the cavity 14 lies between the pairs of transducers 16, 18 and 20, 22. The transducers are approximately 25 mm in diameter and produce 1 MHz (center frequency) broad band signals and are similar to those used in standard non-destructive evaluations.

The transducers 16, 18 are fired simultaneously every 5 milliseconds by pulser—receiver boxes, 24 and 26, respectively (typically Panametrics 5052 UA and Panametrics 5058 PR) which are also connected to the corresponding receiver transducers, 20 and 22. Once every 5 minutes, the P and S signals are fed sequentially via a switch, 28 (which may be an HP59037a RF switch) into an automatic gain control system 30 (such as one manufactured by Wavetek). The attenuated signals are output to an amplifier, 32, (typically, a Panametrics 5052 VA) and then via a low pass filter, 34 (manufactured by TSI, for example) to oscilloscope display, 36, (Tektronix 7854) and digitized, 38 (Tektronix RTD-710) and stored on a computer, 51 (Micro VAX) via GPIB Bus, 50.

Figure 2:
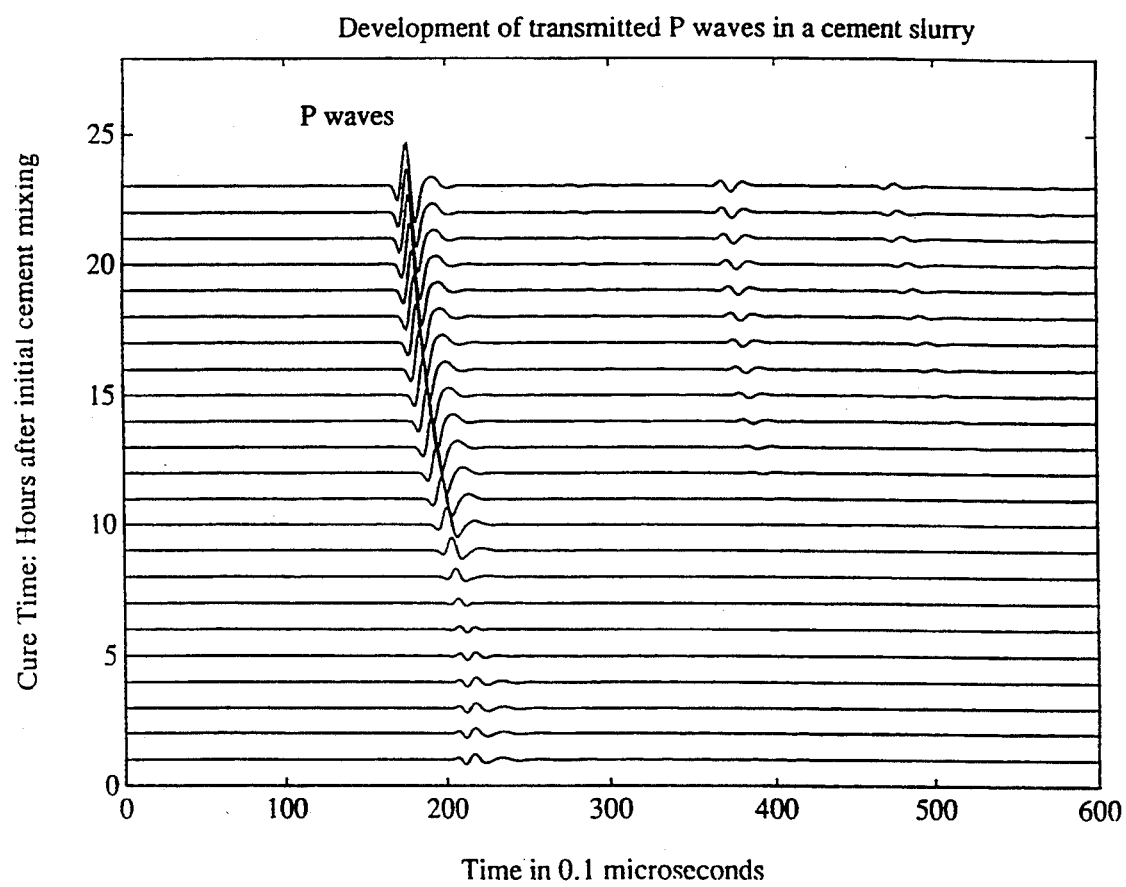
FIG. 2 shows the development of transmitted P waves in a cement slurry.
Figure 3A:
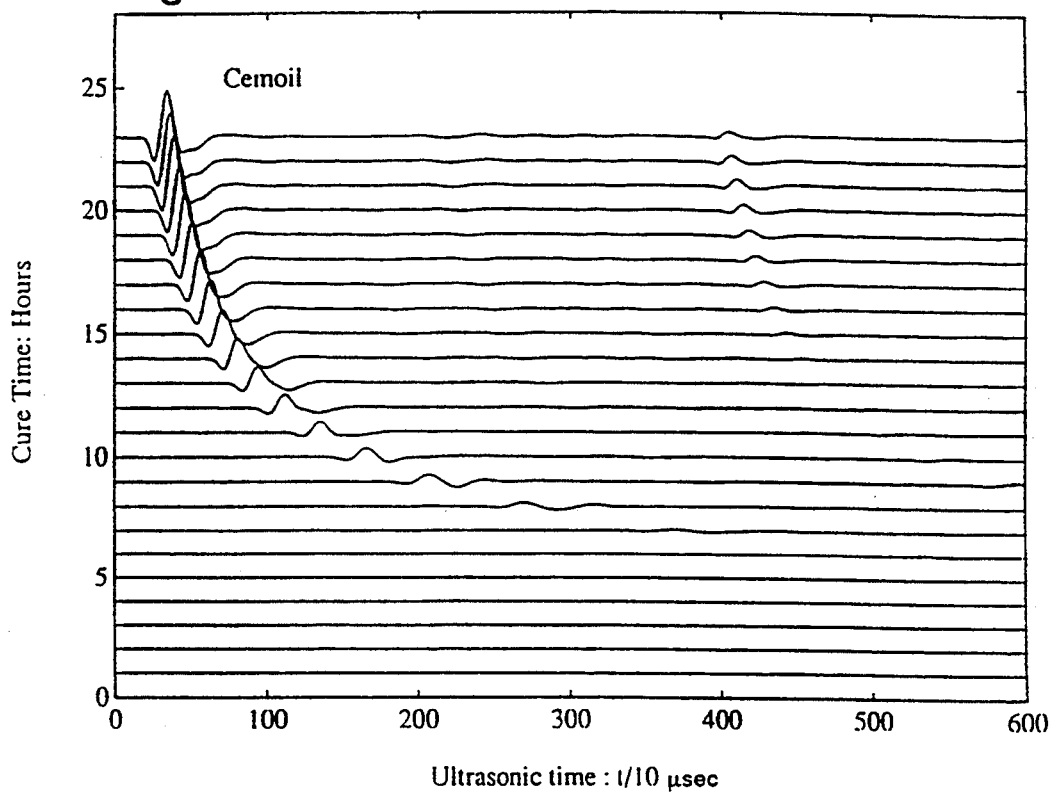
FIG. 3(a) shows a plot of cure time in hours against ultrasonic time (t/10) per micro-second for shear waveforms for a Cemoil cement slurry.
Figure 3B:
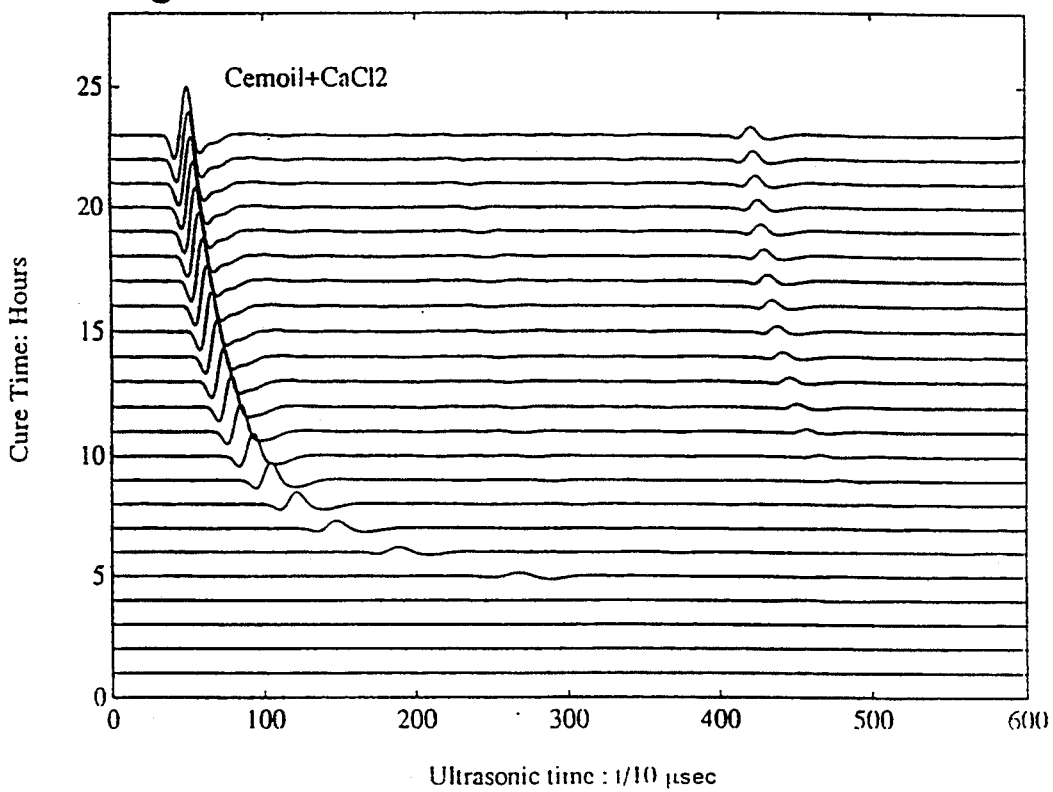
FIG. 3(b) shows the corresponding trace to FIG. 3(a) for a CaCl$_2$ accelerated Cemoil slurry.
Figure 3C:
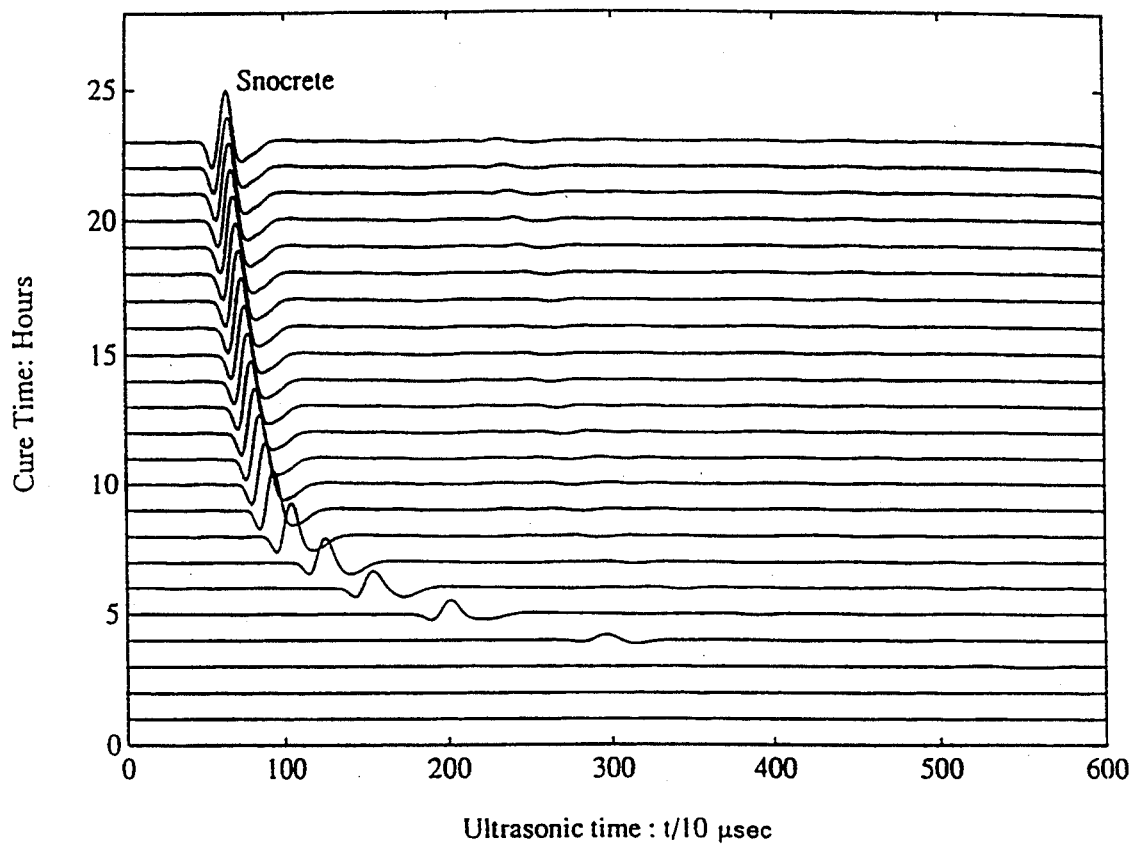
FIG. 3(c) shows the corresponding trace to FIG. 3(a) for a rapid thickening Snocrete slurry.

In use, the cement slurry is mixed in accordance with API SPEC-10 for class H cement (or whatever class is to be investigated), optionally degassed in a vacuum chamber, and poured into the cavity 14 such that it is completely full. The measurements outlined above are then made and the P and S waveforms collected over a 23 hour period are shown in FIGS. 2 and 3. The P wave signal can be easily identified in the first waveform at one hour of cure time. As the cure time increases, the P wave signal moves to shorter acquisition time indicating that its velocity is increasing. By contrast, the S wave signal in FIG. 3(a) does not appear until approximately 7 hours after measurement commences. The appearance of the signal is distinctive and is related to the setting time of the slurry. Once it appears, the velocity of the S wave signals increases as the cement sets further. This coincides with an increase in velocity of the P wave signal. It is believed that the S wave signal only appears after the slurry, which initially comprises solid granular particles suspended in a complex slurry fluid, evolves such that the hydrating solid component forms a percolating, connected network and at this threshold the composite mixture can begin to support shear wave propagation.

In FIGS. 3(a), (b) and (c), the apparatus described above is used to test three slurries, a Cemoil slurry, a CaCl$_2$ accelerated Cemoil slurry and a Snocrete slurry. API thickening times for these slurries are 8 hours, 5 hours and 3.5 hours respectively. In FIGS. 3(a–c), the cure time in hours is displayed against the arrival time of the shear wave. In this display the first arrival of a shear wave signal can be seen at roughly 7 hours (3a), 5 hours (3b), and 4 hours (3c), which is consistent with the API thickening times. As indicated above, waveforms are stored at five minute intervals throughout the cure process. When the additional eleven waveforms taken between each of the one hour intervals shown in FIGS. 3 are examined in more detail, final results for the shear wave onset times art 6.25 hours (3a), 4.08 hours (3b), and 3.08 hours (3c). These data are summarized in Table 1.

Figure 4A:
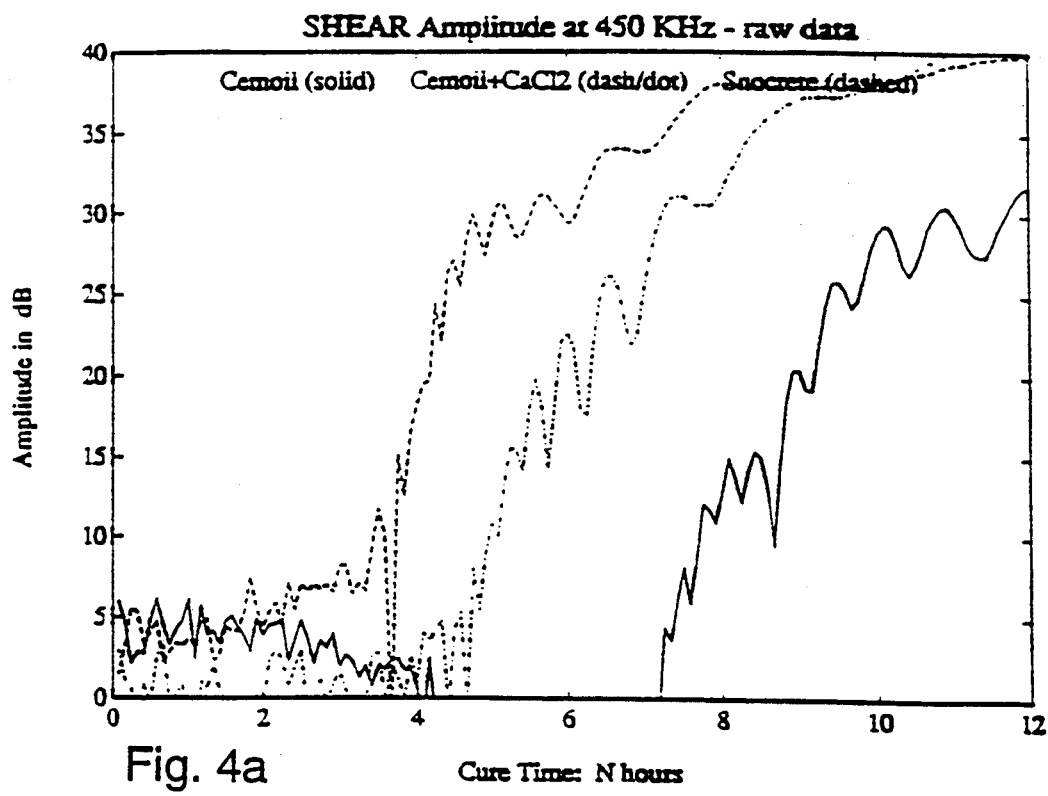
FIG. 4 shows a plot of shear wave energy at 450 KHz (a) and 300 KHz (b) of three slurdes versus cure time.
Figure 4B:
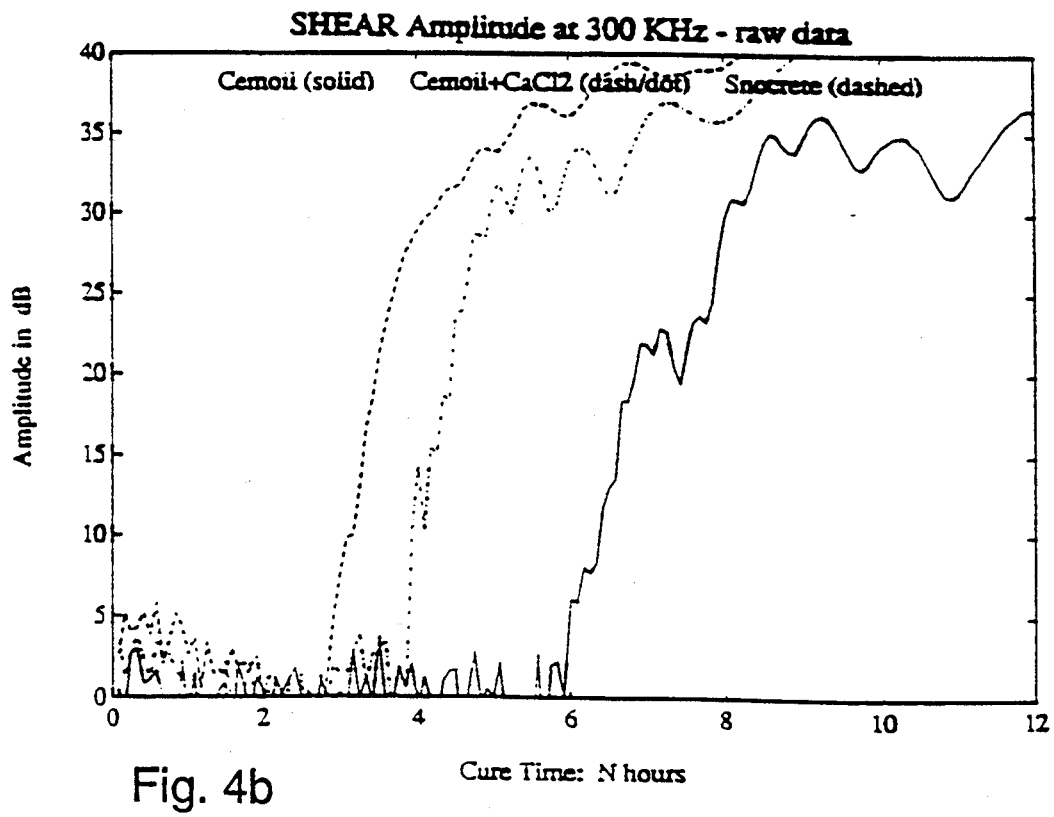

To examine the shear wave onset in more detail, the measured signals can be processed to yield transmitted shear energies. Beginning with a known power spectrum (i.e. the square magnitude of the waveform Fourier transform) the evolution of the transmitted energy as a function of frequency is followed. FIG. 4 shows the transmitted shear energy at 450 KHz and 300 KHz, (frequencies chosen at roughly the center of the late time power spectra) for the same three slurries considered in FIGS. 3. Here, the appearance of shear propagation is seen quite dramatically and the onset times taken from this display (Table 1) are generally in accord with those determined directly from the shear waveforms and, again, correspond well to the API thickening times.

It will be appreciated that the systems described above can be modified to meet practical requirements but has the advantage that it can be operated relatively easily without excessive operator training and can be conducted under conditions simulating field use without undue difficulty.

Figure 5:
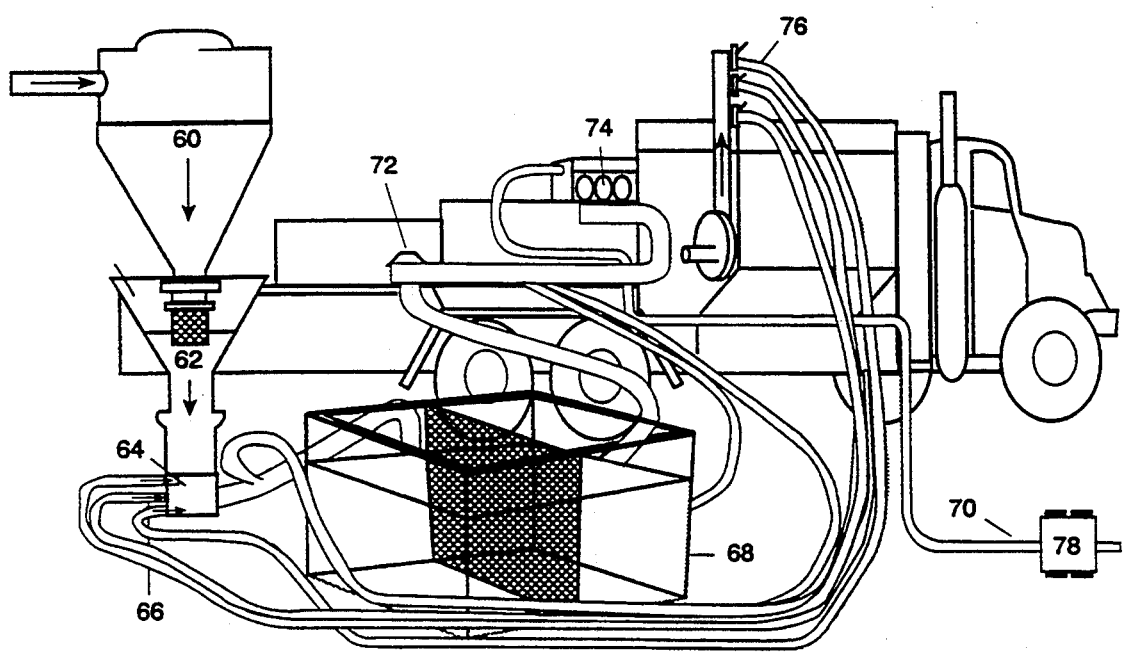
FIG. 5 shows a system for use in a rigsite application of the invention.

The system described above is useful for monitoring cement hydration as a function of temperature, pressure, cement-water ratio, additive concentrations, etc. and thus might be useful in slurry design. The system can be used both in a laboratory or at the rigsite. At the rigsite, the system is for either off-line or on-line cement monitoring. For off-line rigsite use, a sample of slurry is tested either before or at the same time the main slurry is pumped into the well to test the "as mixed" properties of the slurry. For on-line rigsite use, a system such as that shown in FIG. 5 is used in cases where one needs to monitor the slurry as it is being pumped. The system shown is a continuous mixing truck mounted unit comprising a surge can, 60, and hopper, 62, a mixing bowl, 64, with jets, 66, feeding to a slurry tub, 68. This in turn feeds a high pressure line, 70, to the well head (not shown) via a centrifugal pump, 72, and a triplex pump, 74, which are also provided with return lines, 76, to the mixing system. The transmitting and receiving transducers are provided at location, 78, in the line, 70.

It is to be understood that while the devices described throughout the specification are preferred embodiments of the invention, various alternatives, modifications, and equivalents may be used. Therefore, the above description should not be taken as limiting the invention which is defined by the appended claims.

TABLE 1

Summary of results for three oilfield cements. All of the onset times are given in hours.
In the Ratio columns the onset times are normalized to the Cemoil[(1)] results.

| Cement | API Thickening Time | Ratio | Shear Wave Onset Time | Ratio | 450 KHz Onset Time | Ratio | 300 KHz Onset Time | Ratio |
| --- | --- | --- | --- | --- | --- | --- | --- | --- |
| Cemoil[(1)] | 8.0 | 1.00 | 6.25 | 1.00 | 7.10 | 1.00 | 6.00 | 1.00 |
| Cemoil[(2)] 1.4% $C_aCl_2$ | 5.0 | 0.63 | 4.08 | 0.65 | 4.60 | 0.65 | 3.90 | 0.65 |
| Snocrete | 3.5 | 0.44 | 3.08 | 0.49 | 3.70 | 0.52 | 2.90 | 0.48 |

We claim:

1. A method of determining a thickening time for a cement slurry, comprising the steps of:
   (a) preparing said slurry
   (b) generating an acoustic shear wave signal in the slurry;
   (c) monitoring the slurry so as to detect transmission of the acoustic shear wave signal therethrough; and
   (d) determining, from detection of transmission of the acoustic shear wave signal, a time after preparation of the slurry at which shear wave energy is first propagated through the slurry, said time being the thickening time.

2. The method of claim 1, further comprising the steps of:
   (e) generating an acoustic compressional wave signal in the slurry;
   (f) monitoring the slurry so as to detect the velocity of the acoustic compressional wave signal therethrough;
   (g) detecting a time at which the velocity of the acoustic compressional wave signal increases: and
   (h) determining the thickening time from the time of increase in acoustic compressional wave signal velocity as well as from the time at which shear wave energy is first propagated through the slurry.

3. The method of claim 1, wherein the acoustic shear wave signal comprises an ultrasonic signal.

4. The method of claim 3, wherein the ultrasonic signal has a frequency on the order of 1 MHz.

5. The method of claim 1, further comprising the step of degassing the slurry prior to generating and monitoring the acoustic shear wave signal.

6. The method of claim 1, further comprising the step of placing the slurry in a cell having opposed transmitter and receiver transducers thereon for generating and detecting transmission of the acoustic shear wave signal.

7. The method of claim 1, further comprising the step of placing the slurry in a cell having transmitter and receiver transducers on opposite sides thereof for generating and detecting transmission of the acoustic shear wave signal.

8. A method as claimed in claim 1, wherein the time is substantially the same as the API thickening time of the slurry.

9. The method of claim 8, further comprising the steps of:
   (e) generating an acoustic compressional wave signal in the slurry;
   (f) monitoring the slurry so as to detect the velocity of the acoustic compressional wave signal therethrough;
   (g) detecting a time at which the velocity of the acoustic compressional wave signal increases; and
   (h) determining the thickening time from the time of increase in acoustic compressional wave signal velocity as well as from the time at which shear wave energy is first propagated through the slurry.

10. The method of claim 8, wherein the acoustic shear wave signal comprises an ultrasonic signal.

11. The method of claim 10, wherein the ultrasonic signal has a frequency on the order of 1 MHz.

12. The method of claim 8, further comprising the step of degassing the slurry prior to generating and monitoring the acoustic shear wave signal.

13. The method of claim 8, further comprising the step of placing the slurry in a cell having opposed transmitter and receiver transducers thereon for generating and detecting transmission of the acoustic shear wave signal.

14. An apparatus for measuring the thickening time of a cement slurry comprising:
   a body defining a cavity for containing the cement slurry;
   means for generating acoustic signals in the slurry on a first side of the cavity, said acoustic signals including at least one shear wave signal;
   means for receiving acoustic signals from the slurry on a second side of the cavity; and
   means for recording the development of the at least one shear wave signal transmitted through the slurry; and
   means for determining and indicating the thickening time of the slurry based on the development of the at least one shear wave signal.

15. The apparatus of claim 14, wherein the body comprises a closed cell.

16. The apparatus of claim 14, wherein the body comprises a flow line.

17. A method of determining a thickening time for a cement slurry, comprising the steps of:
   (a) preparing said slurry
   (b) generating an acoustic shear wave signal at a first location in the slurry;
   (c) monitoring the slurry at a second location therein so as to detect transmission of the acoustic shear wave signal therethrough; and
   (d) determining, from detection of transmission of the acoustic shear wave signal, a time after preparation of the slurry at which shear wave energy is first propagated through the slurry, said time being the thickening time.

18. A method as claimed in claim 17, wherein step (b) comprises firing a transmitting transducer and step (c) comprises producing a signal with a receiving transducer which receives the acoustic shear wave signal after propagation through the slurry.

19. An apparatus for measuring the thickening time of a cement slurry comprising:
   a body defining a cavity for containing the cement slurry;
   means for generating acoustic shear wave signals in the slurry in the cavity;

means for receiving acoustic shear wave signals from the slurry in the cavity; and means for recording the development of the shear wave signal transmitted through the slurry; and means for determining and indicating the thickening time of the slurry based on the development of the shear wave signal.

* * * * *